(12) United States Patent
Ma et al.

(10) Patent No.: US 11,098,371 B2
(45) Date of Patent: Aug. 24, 2021

(54) METHOD FOR TREATING UROTHELIAL CARCINOMA

(71) Applicants: National Central University, Taoyuan (TW); Huan-Cheng Chang, Taoyuan (TW); DELTA ELECTRONICS, INC., Taoyuan (TW)

(72) Inventors: Nian-Han Ma, Taoyuan (TW); Chien-Lung Chen, New Taipei (TW); Chen-Huan Lin, Taoyuan (TW); An-Lun Li, Taoyuan (TW); Chiu-Chin Huang, Taichung (TW); Chao-Hsiang Chang, Taichung (TW)

(73) Assignees: NATIONAL CENTRAL UNIVERSITY, Taoyuan (TW); Huan-Cheng Chang, Taoyuan (TW); DELTA ELECTRONICS. INC., Taoyuan (TW)

( * ) Notice: Subject to any disclaimer, the term of this patent is extended or adjusted under 35 U.S.C. 154(b) by 63 days.

(21) Appl. No.: 16/460,546

(22) Filed: Jul. 2, 2019

(65) Prior Publication Data
US 2020/0149113 A1 May 14, 2020

(30) Foreign Application Priority Data
Nov. 14, 2018 (TW) ................. 107140464

(51) Int. Cl.
*C12Q 1/6886* (2018.01)
*C12Q 1/6837* (2018.01)
*C12Q 1/6853* (2018.01)

(52) U.S. Cl.
CPC ......... *C12Q 1/6886* (2013.01); *C12Q 1/6837* (2013.01); *C12Q 1/6853* (2013.01); *C12Q 2600/112* (2013.01); *C12Q 2600/158* (2013.01); *C12Q 2600/16* (2013.01); *C12Q 2600/178* (2013.01)

(58) Field of Classification Search
None
See application file for complete search history.

(56) References Cited

FOREIGN PATENT DOCUMENTS

CN 103025384 A 4/2013

OTHER PUBLICATIONS

Zanutto (British Journal of cancer (2014) vol. 110, pp. 1001-1007).*
Eichelser *Clinical Chemistry (2013) vol. 59, pp. 1489-1496).*
Schultz (JAMA (2014) vol. 311, pp. 392-404).*
Ioannidis (BMC Genomics (2018) 19:243).*
Benner et al (Trends in Genetics (2001) vol. 17, pp. 414-418).*
Cheung et al (Nature Genetics, 2003, vol. 33, pp. 422-425).*
Saito-Hisaminato et al. (DNA research (2002) vol. 9, pp. 35-45).*
Chen ( Urologic Oncology (2013)vol. 21, pp. 219-227).*
Enokida (Investigative and Clinical Urology (2016) supplement 1, S60-76).*
Feng (Oncogene (2011) vol. 30, pp. 2242-2251).*
Ghai (Arch Toxicol (2016) vol. 90, pp. 2959-2978).*
Jiang (Int J Cancer (2015) vol. 136, p. 854-862).*
Kang (Japanese Journal of Clinical Oncology (2010) vol. 40, pp. 241-246).*
Chen (American J Physiol Renal Physiol (Mar. 20, 2019) vol. 365, p. F1094-F11027).*

* cited by examiner

*Primary Examiner* — Steven Pohnert
(74) *Attorney, Agent, or Firm* — Muncy, Geissler, Olds & Lowe, P.C.

(57) ABSTRACT

A kit for detecting urothelial carcinoma is provided. The kit includes at least one primer or probe for detecting one or more miRNAs, and the one or more miRNAs are selected from the group consisting of miR-19b-1, miR-636, miR-150, miR-155, miR-183, miR-378, miR-210, miR-487, and combinations thereof. A method for detecting urothelial carcinoma is also provided. The method includes detecting the expression level(s) of one or more miRNAs in a sample of a subject, and the one or more miRNAs are selected from the group consisting of miR-19b-1, miR-636, miR-150, miR-155, miR-183, miR-378, miR-210, miR-487, and combinations thereof.

6 Claims, 5 Drawing Sheets

Specification includes a Sequence Listing.

SEQUENCE LISTING

<160> NUMBER OF SEQ ID NOS: 8

<210> SEQ ID NO 1
<211> LENGTH: 23
<212> TYPE: RNA
<213> ORGANISM: Homo sapiens

<400> SEQUENCE: 1
aguuuugcag guuugcaucc agc                    23

<210> SEQ ID NO 2
<211> LENGTH: 23
<212> TYPE: RNA
<213> ORGANISM: Homo sapiens

<400> SEQUENCE: 2

```
ugugcuugcu cgucccgccc gca                                    23

<210> SEQ ID NO 3
<211> LENGTH: 22
<212> TYPE: RNA
<213> ORGANISM: Homo sapiens

<400> SEQUENCE: 3
ucucccaacc cuuguaccag ug                                     22

<210> SEQ ID NO 4
<211> LENGTH: 23
<212> TYPE: RNA
<213> ORGANISM: Homo sapiens

<400> SEQUENCE: 4
uuaaugcuaa ucgugauagg ggu                                    23

<210> SEQ ID NO 5
<211> LENGTH: 22
<212> TYPE: RNA
<213> ORGANISM: Homo sapiens

<400> SEQUENCE: 5
gugaauuacc gaagggccau aa                                     22

<210> SEQ ID NO 6
<211> LENGTH: 22
<212> TYPE: RNA
<213> ORGANISM: Homo sapiens

<400> SEQUENCE: 6
acuggacuug gagucagaag gc                                     22

<210> SEQ ID NO 7
<211> LENGTH: 22
<212> TYPE: RNA
<213> ORGANISM: Homo sapiens

<400> SEQUENCE: 7
cugugcgugu gacagcggcu ga                                     22

<210> SEQ ID NO 8
<211> LENGTH: 22
<212> TYPE: RNA
<213> ORGANISM: Homo sapiens

<400> SEQUENCE: 8
aaucauacag ggacauccag uu                                     22
```

METHOD FOR TREATING UROTHELIAL CARCINOMA

CROSS-REFERENCE TO RELATED APPLICATION

This application claims priority to Taiwan Application Serial Number 107140464, filed on Nov. 14, 2018, which is herein incorporated by reference in its entirety.

BACKGROUND

Field of Invention

The present invention relates to detection kits and detection methods for cancer-related miRNA(s).

Description of Related Art

MicroRNA (miRNA), an endogenous non-coding RNA molecule of about 19 to 25 nucleotides in length, regulates the expressions of the target genes at the posttranscriptional level by inhibiting the translation of its target mRNAs and/or degrading the mRNAs. The specific expression profile of miRNAs in cancer can be considered as a biological indicator that can be helpful in diagnosis, classification, staging, and prognosis of tumors. The miRNAs detected from a variety of biological fluid samples can be used as markers for non-invasive diagnosis of many cancer types.

Urothelial carcinoma (UC) is a general term for malignant tumors that occur in the urothelium of a patient. The occurrence sites of urothelial carcinoma are throughout the urinary tract, including renal pelvis, ureter, bladder, and urethra. Urothelial carcinoma is derived from diseased urinary epithelial cells and is therefore also referred to as transitional cell carcinoma (TCC). Urothelial carcinoma generally occurs in men, in bladder, and in old age (60 to 70 years old). However, in recent years, the occurring rate of upper urinary tract UC (UCC), e.g., renal pelvis cancer, ureteral cancer, is increasing, and the number of females suffering from UC is also increasing.

At present, the diagnosis of urothelial carcinoma, in addition to medical history querying and pathology examination, includes urine test, urine cytology examination, and urinary tract imaging (e.g., ultrasound, intravenous urinary tract photography, and CT or MR imaging of the abdomen or pelvic cavity). Moreover, for high-risk patients, invasive urinary endoscopy (including cystoscopy and ureteroscopy) is also necessary. The confirmed diagnosis of cancer requires further slicing and pathological microscopic examination to determine the type and malignancy degree of the tumor. The initial symptoms of urothelial carcinoma are not obvious, and patients mainly have hematuria and low back pain. Usually, this cancer is in more advanced stages when the diagnosis is confirmed. Currently, no appropriate tumor marker can be provided for diagnosis and tracking the responses of therapy; this causes late detection and higher mortality.

SUMMARY

In view of the problems above-mentioned, the present invention provides detection kits and detection methods for detecting urothelial carcinoma (UC), which are helpful for diagnosis and tracking therapy of urothelial carcinoma.

One aspect of the present invention provides a detection kit for detecting urothelial carcinoma. The kit includes at least one primer or probe for detecting one or more miRNAs, the one or more miRNAs are selected from the group consisting of miR-19b-1, miR-636, miR-150, miR-155, miR-183, miR-378, miR-210, miR-487, and combinations thereof.

Another aspect of the present invention provides a detection method for detecting urothelial carcinoma. The method includes measuring the expression levels(s) of one or more miRNAs in a sample from a subject, wherein the one or more miRNAs are selected from the group consisting of miR-19b-1, miR-636, miR-150, miR-155, miR-183, miR-378, miR-210, miR-487, and combinations thereof; and evaluating a risk of urothelial carcinoma for the subject.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
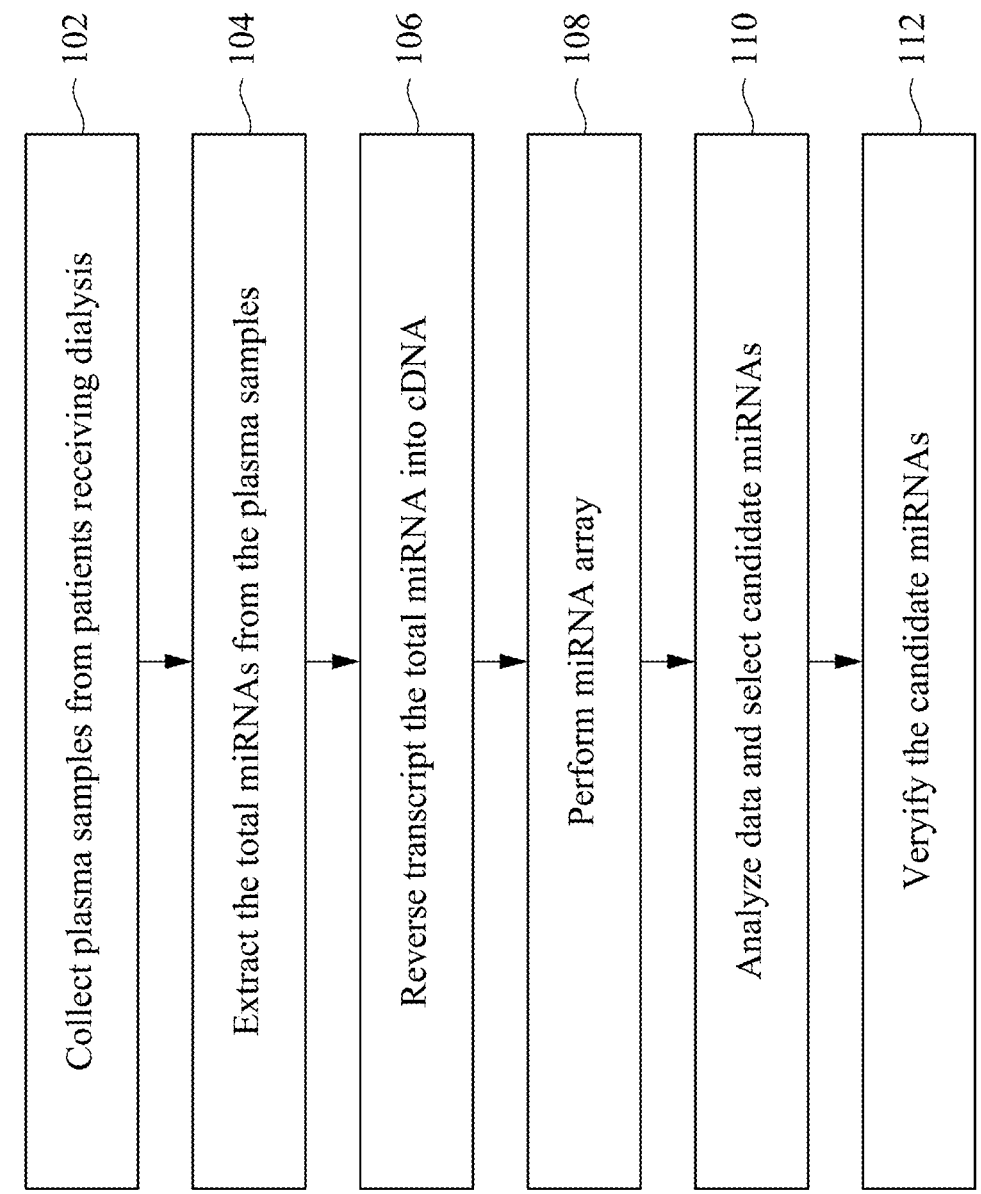
FIG. 1 shows a flow chart of screen miRNAs for detecting urothelial carcinoma in accordance with some experiments of the present invention.

Reference will now be made in detail to the present embodiments of the invention, examples of which are illustrated in the accompanying drawings. Wherever possible, the same reference numbers are used in the drawings and the description to refer to the same or like parts.

As used in this specification and the appended claims, the singular forms, "a", "an", and "the" refers to at least one or more than one referents unless the content clearly dictates otherwise. Further, the term "or" is generally used in its meaning, "and/or", unless the content clearly dictates otherwise.

The incidence rate of urothelial carcinoma in the general population is not high, but in patients who receive dialysis treatment, the incidence rate is high, and the recurrence rate in these patients is also higher. In addition, it is noted that in Taiwan, most urinary tract tumors are urothelial carcinoma, but in other countries, most urinary tract tumors are renal cancer.

The basic treatment for urothelial carcinoma is total ureteral resection surgery on the affected side. At present, most of the surgeries are minimally invasive surgery (laparoscopic surgery or Da Vinci robotic arm assisted surgery), which can make better wound appearance, less bleeding and pain, and faster recovery compared to traditional surgery. When a patient has hematuria, as long as no delay in the diagnosis, the five-year survival rate of the patient may reach 90%. If the patient has a special condition, such as only one kidney or kidney on the other side has poor function, and it is expected that the standard renal total resection will immediately result in dialysis, local resection can be considered to keep the kidney. In addition, this cancer also has good responses to chemotherapy and radiation therapy. Therefore, the above two therapies will be combined before and after the surgery to achieve the best results of the treatment. For example, patients with Stage III or Stage IV tumors will be administrated chemotherapy to reduce the dimension of the tumors and then be administrated surgery for achieving a higher chance of complete cure.

Therefore, if urothelial carcinoma can be detected earlier, the survival rate of the patients can be improved.

Some experiments of this disclosure relate to long term follow-up studies in patients receiving dialysis, because the incidence rate of urothelial carcinoma is higher among these patients. The study includes clinical, biochemistry, blood and imaging examinations, changes of miRNA expression profiles in blood, urine, and tissue, the occurrence and progression of disease and tumor, and the tracking and evaluation of the treatment. Further, we analyze and identify the role of miRNA in urothelial carcinoma.

FIG. 1 illustrates a flow chart for screening miRNAs associated with urothelial carcinoma.

In step 102 of method 100, plasma samples from patients receiving dialysis were collected. Because of the high incidence of urothelial carcinoma among these patients, the expressions of miRNAs in patients without urothelial carcinoma and in patients with urothelial carcinoma were compared to identify the difference of miRNA expression profile between the two patient groups.

Then, in step 104, the total miRNAs were extracted from the plasma samples. miRNA is very stable in human tissue and cell samples, and it is not easily degraded. miRNA can be detected in many body fluids such as blood, saliva, and urine. Some experiments in the present invention relate to isolating plasma from blood samples of patients, then the miRNAs in the plasma were examined.

Then, in step 106, reverse transcription of total miRNAs into cDNAs was performed.

Then, in step 108, miRNA array was performed. The cDNAs were examined on chips of miRNA array to measure the expression levels of the detectable miRNAs for the chips. For example, TaqMan® Array Human MicroRNA A Cards v2.0 can be used to detect about three thousand human miRNAs.

Then, in step 110, the data are analyzed, and the candidate genes were selected. According to miRNA array results, specific miRNAs with significant differences between non-UC and UC patients can be identified. For example, some specific miRNAs are highly expressed in samples from UC patients; some other specific miRNAs are expressed lower in UC patients; these miRNAs can be used as candidate genes for detecting UC.

Then, in step 112 of method 100, the candidate genes were verified. These candidate genes were verified, for example, by performing real-time PCR quantification experiments to measure the expression levels of the respective genes in non-UC and UC patients. In addition, the samples from a cohort of new subjects were also examined for verification.

In the present invention, ROC curve is used to assess the specificity and accuracy for detection of urothelial carcinoma. For example, software "prism" was used to draw the ROC curve. The input data were the normalized expression levels of miRNAs; the default setting values were used in calculating, followed by selecting the value corresponding to the most likelihood ratio as cut off; then the cut off was used to obtain the specificity and the accuracy.

In addition, in some experiments, the process also included testing different combinations of miRNAs, performing numerical calculations on the expression of each miRNA, and establishing a model formula for assessing the risk of urothelial carcinoma by multivariate logistic regression analysis (e.g., Logis regression analysis).

Experimental Examples

Collection of Patient Samples

The samples were from patients receiving long-term dialysis (dialysis treatment for over three months) in LICNI hospital. 100 patients were selected for a 3-year follow-up study, including basic miRNA analysis every year, monthly regular biochemical blood test, semi-annual immunological tests, and annual radiographic imaging examination to analyze the association between miRNA(s) and urothelial carcinoma. In addition, for patients having tumors, their miRNA expression profiles and antibody levels were analyzed to find the differences between non-UC and UC patients. The differences can be evaluated whether they can be markers for tumor diagnosis, evaluating therapy and prognosis, and tracking therapy.

The total miRNAs in each of the patients' plasma were extracted conventionally and were reverse transcribed into cDNAs.

Reverse Transcription and miRNA Array

After the quality of the total miRNAs extracted from the sample had been confirmed, miRNA array was carried out. Steps of miRNA array include: 600 ng miRNA was reverse transcribed according to the protocol of the manufacturer of TaqMan MicroRNA Transcriptase; then the miRNA array was carried out using the reverse transcription product (cDNA) and according to the protocol of the manufacturer of TaqMan® Array Human MicroRNA A Cards v2.0.

Data Analysis and Validation of Candidate Genes

Two methods were used to normalize the data. In the first method, the data were normalized through RNU6 (U6 small nuclear RNA). The CT value of RNU6 was used as the reference in the miRNA array. The expression levels of various miRNAs were obtained through the formula of $2^{-\Delta CT}$, wherein $\Delta CT$ is the CT value of the target miRNA minus the CT value of RNU6. In the second method, the averages of the CT values of all detected miRNAs were used as the reference, and the expression levels of the various miRNAs were obtained through the formula of $2^{-\Delta CT}$, wherein the $\Delta CT$ is "the CT value of the target miRNA minus the average CT value."

After data collection, software "R language" was used to perform cluster analysis and calculate the magnification. Diagrams were drawn by using the "plot" function of the "gplots" package of software "R language". In the diagrams, the horizontal axis (x-axis) is the magnification or difference. The calculation of the magnification or difference was performed through the average data of each group, using patients with UC as an experimental group, and patients without UC (non-UC) as a control group. The magnification or difference was obtained by dividing the data of the experimental group (UC) by the data of the control group (non-UC). The vertical axis (y-axis) showed the P value according to T-test and processed by −log 10, wherein the T-test was performed using the "t. test" function of software "R language".

In an experiment, respective samples from 8 patients undergoing dialysis treatment were used to perform miRNA arrays. Among them, 4 patients had urothelial carcinoma and the other 4 patients did not develop urothelial carcinoma. Table 1 below shows the characteristics of the 8 patients.

TABLE 1

|  |  | UC patients | | | Non-UC patients | | | P value |
|---|---|---|---|---|---|---|---|---|
|  |  | Number | Average | Standard deviation | Number | Average | Standard deviation |  |
| Age |  | 4 | 67.5 | 7.935 | 4 | 63.25 | 4.38 | 0.072 |
| Number of years of dialysis treatment |  | 4 | 13.49 | 3.92 | 4 | 8.25 | 3.15 | 0.12 |
| Gender | Female |  | 3 |  |  | 3 |  | 1 |
|  | Male |  | 1 |  |  | 1 |  |  |
| Cancer stage | Lower |  | 2 |  |  |  |  |  |
|  | Higher |  | 2 |  |  |  |  |  |

After the miRNA data of the 8 patients were analyzed, 8 miRNAs were selected: miR-19b-1, miR-183, miR-636, miR-155, miR-378, miR-487a, miR-150, and miR-210.

Referring to Table 2 below, the difference in the expression levels can be classified into 3 types: unique expression means the miRNA only expressed in UC patients or only in non-UC patients; single analysis means there was a significant difference in the expression levels (normalized based on the CT value of U6-snRNA) between UC patients and non-UC patients; ratio analysis means there was a significant difference in the ratio of miRNA expression levels (the ratio of two miRNAs normalized based on the CT value of U6-snRNA) between UC patients and non-UC patients.

TABLE 2

| Screen criteria | miRNA gene |
|---|---|
| Unique | miR-19b-1 |
|  | miR-183 |
| Single analysis | miR-636 |
| Ratio analysis | miR-155 |
|  | miR-378 |
|  | miR-487 |
|  | miR-150 |
|  | miR-210 |

To further validate the results of the initial screening, new subjects were enrolled for validation. Samples of 52 subjects were collected, and the plasma of the samples was respectively isolated. The total miRNAs in this plasma was then extracted, and reverse transcription reaction was carried out. Then the expression levels of the 8 miRNAs mentioned-above in the reverse-transcribed samples were measured using Taqman miRNA assay (Applied Biosystems).

Table 3 below shows the characteristics of the 52 subjects.

|  |  | UC patients | | | Non-UC patients | | | P-value |
|---|---|---|---|---|---|---|---|---|
|  |  | Number | Average | Standard deviation | Number | Average | Standard deviation |  |
| Age |  | 15 | 70.9 | 7.14 | 37 | 66.5 | 9.25 | 0.082 |
| Number of years of dialysis treatment |  | 7 | 13.49 | 3.92 | 37 | 11.74 | 5.26 | 0.57 |
| Gender | Female |  | 10 |  |  | 22 |  | 0.76 |
|  | Male |  | 5 |  |  | 15 |  |  |
| Cancer stage | Lower |  | 2 |  |  |  |  |  |
|  | Higher |  | 13 |  |  |  |  |  |

40

Then, real-time PCR was performed and the expression data of the above mentioned 8 miRNAs were acquired. Then the expression level data were calculated to confirm that some miRNA ratios (ratio of two miRNA expression levels, e.g., miR-155/miR-150) were different between UC and non-UC patients. The ratios of the miRNA expression levels can help assess the risk of urothelial carcinoma.

Table 4 below shows some miRNA ratios which are different between UC and non-UC patients. The areas under curve (AUCs) of ROC curve of the miRNA ratios were at least more than 0.6.

TABLE 4

|  | AUC | P-value |
|---|---|---|
| miR-155/miR-150 | 0.751 | 0.004857 |
| miR-378/miR-150 | 0.714 | 0.01673 |
| miR-636/miR-150 | 0.701 | 0.02436 |
| miR-150/miR-210 | 0.685 | 0.03848 |
| miR-19b-1/miR-378 | 0.676 | 0.04897 |
| miR-19b-1/miR-487a | 0.668 | 0.2200 |
| miR-210/miR-183 | 0.658 | 0.012 |
| miR-19b-1/miR-155 | 0.656 | 0.215721 |
| miR-487a/miR-155 | 0.65 | 0.218336 |
| miR-636/miR-487a | 0.644 | 0.098878 |
| miR-210/miR-487a | 0.641 | 0.136675 |

FIGS. 2A through 2E respectively show 5 ratios in the table 3 mentioned above in non-UC patients and in UC patients. The "*" and "**" indicates the difference between the two groups is significant. "*" indicates the p-value is smaller than 0.05, and "**" indicates the p value is smaller than 0.01. "•" indicates the outlier value.

Figures 2A, 2B, 2C:
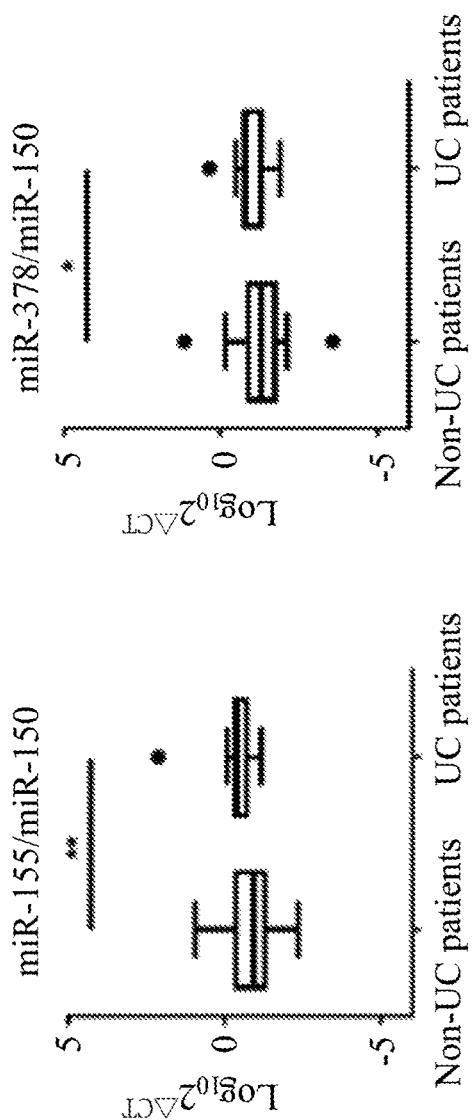
FIG. 2A shows the ratios of miR-155/miR-150 in samples from non-urothelial carcinoma (non-UC) and urothelial carcinoma (UC) patients in accordance with some experiments of the present invention.
FIG. 2B shows the ratios of miR-378/miR-150 in samples from non-UC and UC patients in accordance with some experiments of the present invention.
FIG. 2C shows the ratios of miR-636/miR-150 in samples from non-UC and UC patients in accordance with some experiments of the present invention.

Referring to FIG. 2A, miR-155/miR-150 in UC patients were significantly higher than that in non-UC patients.

Referring to FIG. 2B, miR-378/miR-150 in UC patients were significantly higher than that in non-UC patients.

Referring to FIG. 2C, miR-636/miR-150 in UC patients were significantly higher than that in non-UC patients.

Figures 2D, 2E:
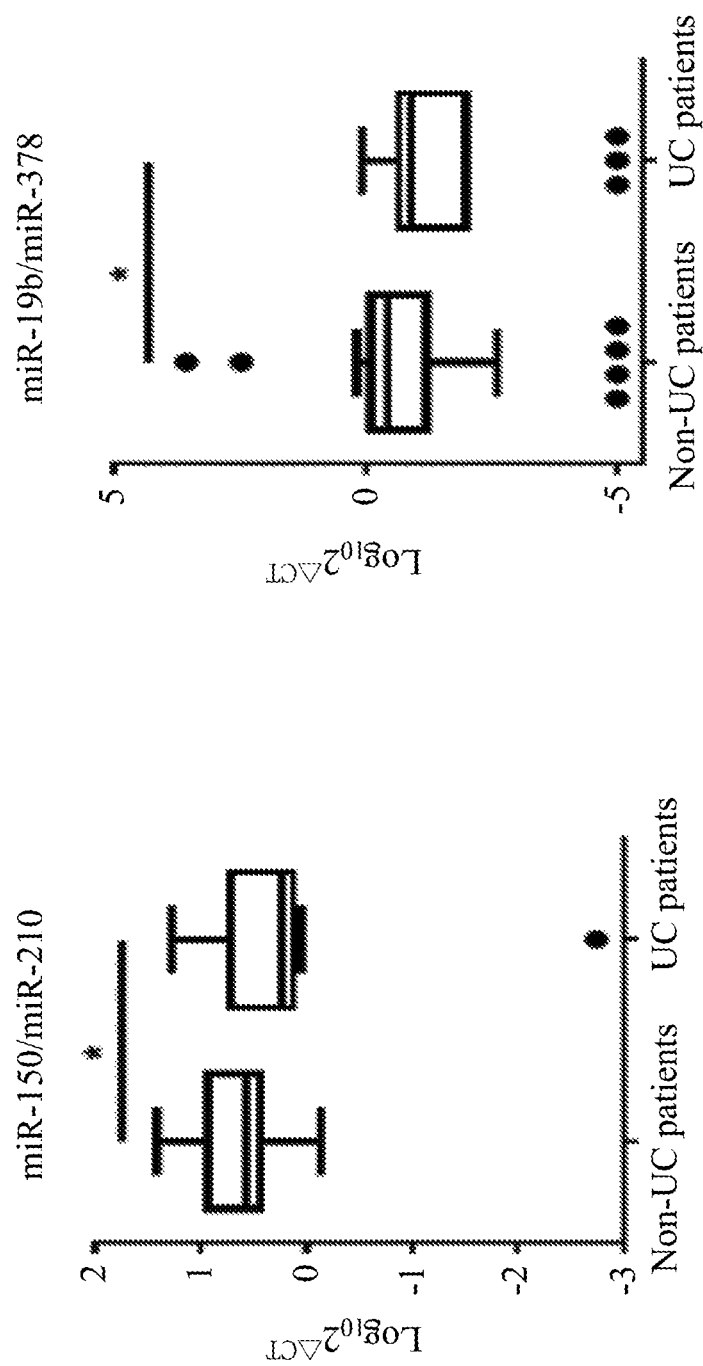
FIG. 2D shows the ratios of miR-150/miR-210 in samples from non-UC and UC patients in accordance with some experiments of the present invention.
FIG. 2E shows the ratios of miR-19b-1/miR-378 in samples from non-UC and UC patients in accordance with some experiments of the present invention.

Referring to FIG. 2D, miR-150/miR-210 in UC patients were significantly lower than that in non-UC patients.

Referring to FIG. 2E, the miR-19b-1/miR-378 ratio in UC patients were significantly lower in non-UC patients.

Then, these specific miRNA ratios were used in multivariate regression analysis, e.g., logistic regression analysis, to set up a model formula for detecting UC. The formula is as follows:

$$\text{Logit } P = -4.762 + (2.852 \times \text{miR-155/miR-150}) + (0.337 \times \text{miR-378/miR-150}) + (1.276 \times \text{miR-636/miR-150}) + (1.578 \times \text{miR-19}b\text{-1/miR-378})$$

Figures 3A, 3B, 3C:
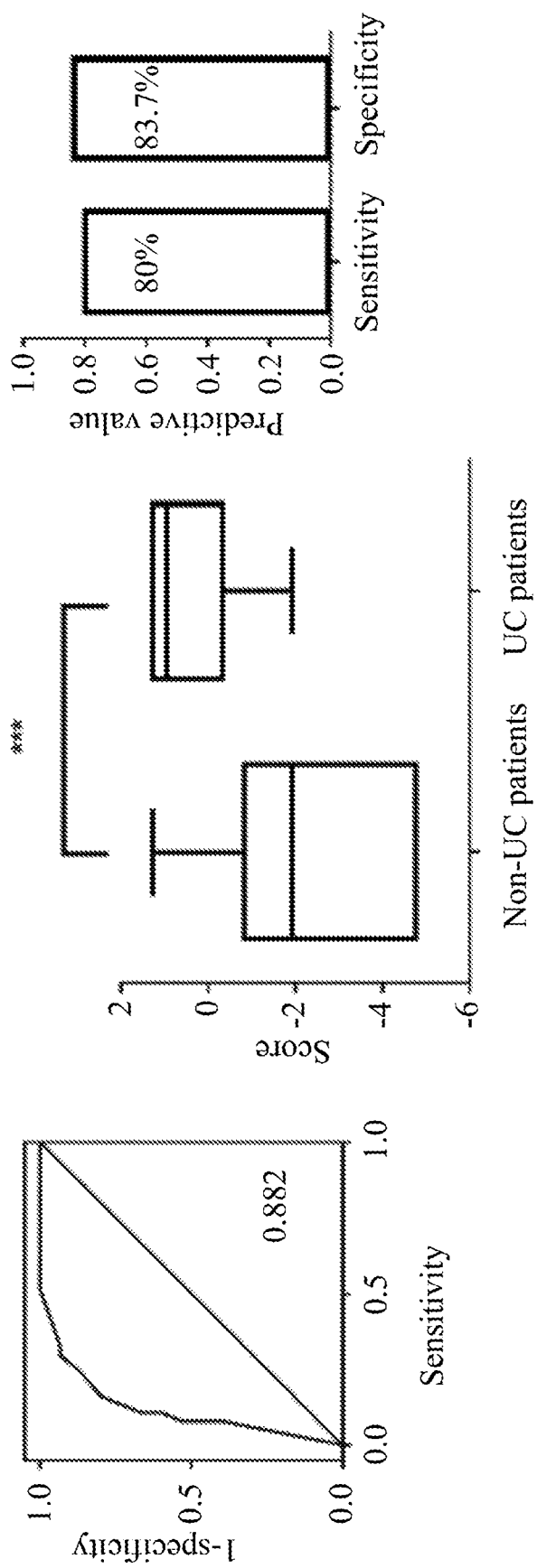
FIG. 3A shows the receiver-operating-characteristic (ROC) curve in accordance with some experiments of the present invention.
FIG. 3B shows the risk-related scores of non-UC and UC patients in accordance with some experiments of the present invention.
FIG. 3C shows the sensitivity and specificity of a combination of miRNAs for detecting urothelial carcinoma in accordance with some experiments of the present invention.

FIG. 3A shows the ROC curve based on the model formula and the data of the patients of table 3. The closer the AUC in the ROC plot is to 1, the higher the sensitivity and specificity. FIG. 3A shows that the AUC was 0.882; therefore, the method based on the model formula of the present invention resulting in assessment with high accuracy.

Referring to FIG. 3B, the signature score obtained based on the model formula was significantly higher in UC patients than that in non-UC patients.

Referring to FIG. 3C, when the model formula was applied in detecting urothelial carcinoma, the sensitivity was 80%, and the specificity was 83.7%.

Accordingly, from the above experimental results in the present invention, the expression levels of miR-19b-1, miR-183, miR-636, miR-155, miR-378, and miR-150, miR-210, or miR-487 can be markers for detecting urothelial carcinoma, because their expression levels significantly associated with urothelial carcinoma. Also, for example, a combination of these miRNA expressions, or a ratio of two miRNAs can be utilized, because the data show significant differences between the UC and the non-UC patients.

In the present invention, the scores based on the ratios of miR-155/miR-150, miR-378/miR-150, miR-636/mi R-150, miR-19b-1/miR-378, and the model formula have more significant differences between the UC and the non-UC patients.

Accordingly, the disclosure provides that miR-19b-1, miR-183, miR-636, miR-155, miR-378, miR-150, miR-210, or miR-487 as detection markers for urothelial carcinoma, so that these markers can be used to develop kits and methods for detecting urothelial carcinoma. Then, the expression levels of these miRNAs can be measured in patients suspected of having urothelial carcinoma or in patients receiving cancer therapy for monitoring the responses of the therapy or evaluating tumor recurrence.

In some embodiments of the present invention, the kit for urothelial carcinoma detection includes primers or probes for detecting one or more miRNAs, the one or more miRNAs are selected from the group consisting of miR-19b-1, miR-636, miR-150, miR-155, miR-183, miR-378, miR-210, miR-487, and combinations thereof.

In some embodiments of the kit, the miRNAs to be detected is at least 2, 3, 4, 5, 6, 7, or all of the group consisting of miR-19b-1, miR-636, miR-150, miR-155, miR-183, miR-378, miR-210, and miR-487.

In some embodiments, the miRNAs to be detected in the kit are miR-19b-1, miR-636, miR-150, miR-155, miR-183, and miR-378.

In some embodiments of the kit, the miRNAs to be detected are miR-19b-1, miR-636, miR-150, miR-155, and miR-378.

In some embodiments, the kit can be used to detect urothelial carcinoma, such as renal pelvic cancer, ureteral cancer, bladder cancer, and urethral cancer.

In some embodiments, the primer or probe specifically binds to the RT product of the miRNAs, wherein the sequence of miR-19b-1 is SEQ ID NO: 1, and the sequence of miR-636 is SEQ ID NO: 2, the sequence of miR-150 is SEQ ID NO:3, the sequence of miR-155 is SEQ ID NO:4, the sequence of miR-183 is SEQ ID NO:5, the sequence of miR-378 is SEQ ID NO:6, the sequence of miR-210 For SEQ ID NO: 7, and the sequence of miR-487 is SEQ ID NO: 8.

In some embodiments, wherein the miR-19b-1 is hsa-miR-19b-3p: miR-636 is hsa-miR-636; miR-150 is hsa-miR-150-5p, miR-155 is hsa-miR-155-5p; miR-183 is hsa-miR-183-5p; miR-378 is hsa-miR-378a-5p; miR-210 is hsa-miR-210-3p; miR-487 is hsa-miR-487a-3p.

In some embodiments, the kit may further include reagents commonly used in PCR reactions, such as buffers, dNTP, MgCl2, pure water, Taq enzymes, etc. The kit may further include standards and/or controls.

In some embodiments, the probe or primer in the detection kit can be attached to a solid carrier, such as a chip.

In some embodiments of the present invention, the method of detecting urothelial carcinoma includes measuring the expression level of a set of miRNA, the set of miRNA is selected from the group consisting of miR-19b-1, miR-636, miR-150, miR-155, miR-183, miR-378, miR-210, miR-487, and combinations thereof.

In some embodiment, the method further includes evaluating the risk of urothelial carcinoma in the subjects.

In some embodiments of the present invention, the use of a detection kit for the diagnosis of UC is provided. The kit includes reagents for measuring the expression level of a set of miRNA, the set of miRNA is selected from the group consisting of miR-19b-1, miR-636, miR-150, miR-155, miR-183, miR-378, miR-210, miR-487, and combinations thereof.

Figure 4:
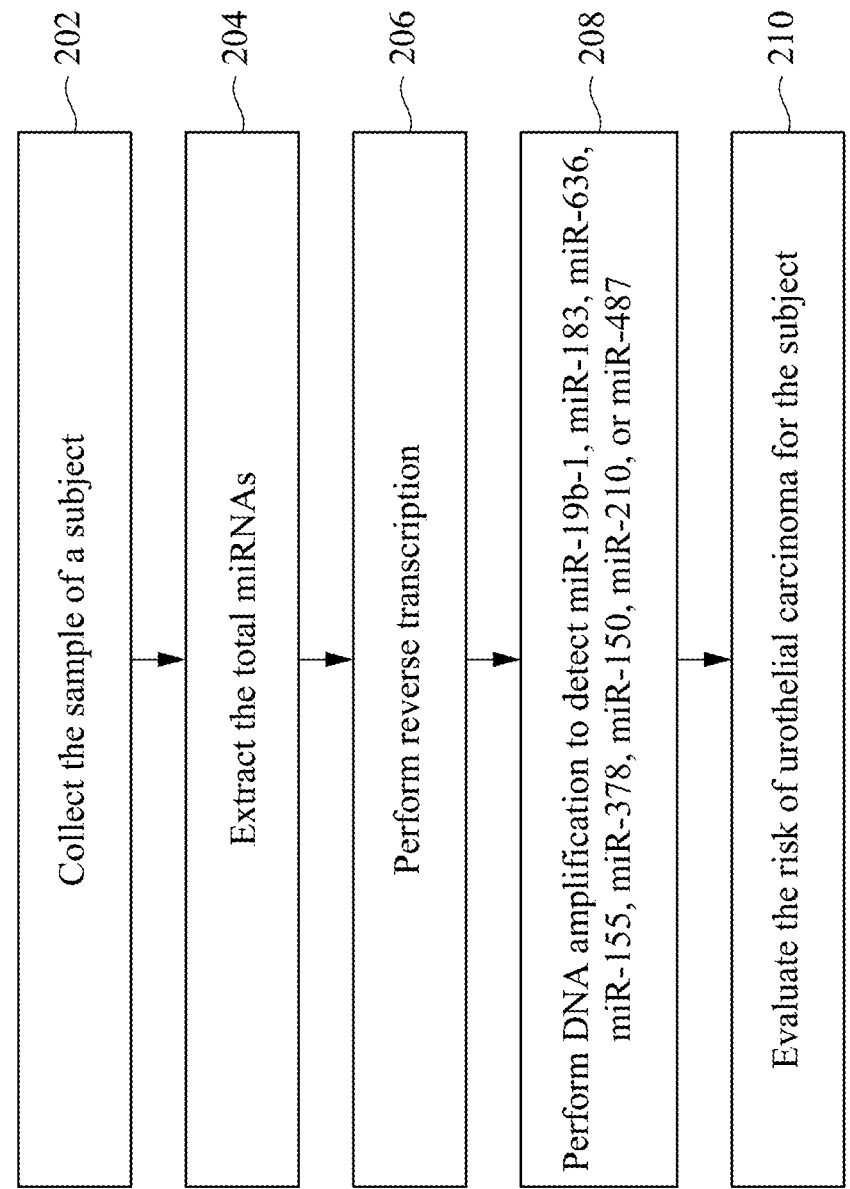
FIG. 4 shows the flow chart of the detection method for urothelial carcinoma in accordance with some embodiments of the present invention.

FIG. 4 shows a flow chart for detecting urothelial carcinoma according to some embodiments. In the first step 202 of method 200, the respective samples of the subjects are collected. The types of the samples may be, for example, blood, serum, plasma, urine, saliva, ascites fluid, or the like. Then in step 202, total miRNAs are extracted from each of the samples. In step 206, reverse transcription is performed, so that the total miRNAs are transcribed into complementary DNAs (cDNAs).

In step 208 of method 200, DNA amplification is carried out (e.g., PCR reaction, such as real-time PCR), and the miRNA to be detected is selected from the group consisting of miR-19b-1, miR-636, miR-150, miR-155, miR-183, miR-378, miR-210, miR-487, and combinations thereof.

In step 210 of method 210, the risk of urothelial carcinoma for the subject is assessed. Since the expression levels of the detected miRNAs can be markers of urothelial carcinoma, the miRNAs can be used to assess whether the subject is likely to have urothelial carcinoma.

In some embodiments, at least two, three, four, five, six, seven, or all of the group consisting of miR-19b-1, miR-636, miR-150, miR-155, miR-183, miR-378, miR-210, miR-487 are detected.

In some embodiments, the miRNAs to be detected are miR-19b-1, miR-636, miR-150, miR-155, miR-183, and miR-378.

In some embodiments, the miRNAs to be detected are miR-19b-1, miR-636, miR-150, miR-155, and miR-378.

In some embodiments, the detection method can be used to detect urothelial carcinoma, such as renal pelvic cancer, ureteral cancer, bladder cancer, and urethral cancer.

In some embodiments of the detection method, measuring miRNA expression in the sample of a subject includes: adding a probe or primer that specifically binds to the reverse transcription product of the miRNA, and performing DNA amplification reaction, e.g., PCR reaction.

In some embodiments of the detection method, assessing the risk of urothelial carcinoma for the subject includes calculating a score of the subject based on the expression levels of the miRNAs.

In some embodiments of the detection method, calculating the score includes obtaining a risk-related score based on the measured expression levels of the miRNAs and numerical calculation. The score can be used to assess the risk of urothelial carcinoma for the subject.

In some embodiments, calculating the score is based on the ratio of the expression levels of two miRNAs.

In some embodiment, multiple sets of miRNA expression ratio are used to calculate the score.

In some embodiments, the score of risk is calculated using the value of miR-150/miR-155, miR-378/miR-150, miR-636/miR-150, or miR-19b-1/miR-378. For example, when the value of miR-150/miR-155 is <7.930, it indicates that the subject is at risk of UC, and the conversion score is set to 1 point; when the value of miR-150/miR-378 is <7.145, it indicates that the subject is at risk of UC, and the conversion score is set to 1 point; when the value of miR-150/miR-138 is <181.4, it indicates that the subject is at risk of UC, and the conversion score is set to 1 point; when the value of miR-19b-1/miR-183 is <1.627, it indicates that the subject is at risk of UC, and the conversion score is set to 1 point. Thereafter, the higher the subject's total conversion score, the higher the likelihood of UC.

In some embodiments, calculating the score of the subject includes calculating the values of miR-155/miR-150, miR-378/miR-150, miR-636/miR-150, miR-19b-1/miR-378, or miR-210/miR-183.

In some embodiments, calculating the score of the subject includes calculating the values of miR-155/miR-150, miR-378/miR-150, miR-636/miR-150, miR-19b-1/miR-378, and miR-210/miR-183.

In some embodiments, wherein calculating the score of the subject further includes obtaining a score value by a formula, wherein the formula is:

$$\text{Logit } P = -4.762 + (2.852 \times \text{miR-155/miR-150}) + (0.337 \times \text{miR-378/miR-150}) + (1.276 \times \text{miR-636/miR-150}) + (1.578 \times \text{miR-19}b\text{-1/miR-378})$$

In some embodiments, the subject is at higher risk of UC, such as a patient receiving dialysis treatment.

In some embodiments, if the subject's risk score is positive, such as above 0, 0.5, 1, or higher, the subject has a higher risk of UC; if the subject's risk score is negative, such as below −2, −3, −4, −5, or lower, the subject is at lower risk of UC.

In some embodiments of the detection method, the sample is blood, serum, plasma, urine, saliva, or ascites fluid.

In some embodiments, comparing to detecting one miRNA, detecting a group consisting of multiple miRNAs can enhance the sensitivity and specificity of UC diagnosis.

Embodiments of the present invention can be used for better monitoring or predicting urothelial carcinoma in patients at risk, such as patients receiving dialysis treatment. Compared with traditional tumor makers, miRNAs in body fluids (such as plasma) as markers of urothelial carcinoma have advantages, such as good stability, non-invasiveness, and high sensitivity and specificity.

The kits and method provided in the present invention can be applied in clinics for diagnosing and tracking urothelial carcinoma.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method for treating urothelial carcinoma in a human comprising steps of: measuring expression levels of miRNAs in a sample of the human, said miRNAs are selected from the group consisting of miR-19b-1, miR-636, miR-150, miR-155, miR-183, miR-378, miR-210, miR-487, and combinations thereof, wherein the sample comprises blood, serum, or plasma; and evaluating a risk of urothelial carcinoma for the human comprising obtaining a score by calculating a ratio of miR-155 to miR-150, a ratio of miR-378 to miR-150, a ratio of miR-636 to miR-150, a ratio of miR-150 to miR-210, a ratio of miR-19b-1 to miR-378, a ratio of miR-210 to miR-183, or a combination thereof, wherein when the ratio of miR-155 to miR-150, the ratio of miR-378 to miR-150, the ratio of miR-636 to miR-150, or the combination thereof in the sample of the human is higher than that of a control, and/or when the ratio of miR-150 to miR-210, the ratio of miR-19b-1 to miR-378, or the combination thereof in the sample of the human is lower than that of the control, the human is at risk of urothelial carcinoma, wherein the control is a non-urothelial carcinoma human's sample comprising blood, serum, or plasma; and administrating a urothelial carcinoma for treatment to the human who is at risk of urothelial carcinoma with a suitable therapy, wherein the treatment is an ureteral resection surgery, chemotherapy, radiation therapy, or a combination thereof.

2. The method of claim 1, wherein said miRNAs are the miR-19b-1, the miR-636, the miR-150, the miR-155, and the miR-378.

3. The method of claim 1, wherein measuring the expression level(s) levels of the miRNAs in the sample of the human comprises steps of:
adding at least one probe or primer that specifically binds to reverse transcription products of the miRNAs; and
performing a DNA amplification reaction.

4. The method of claim 1, wherein evaluating a risk of urothelial carcinoma for the human further comprises obtaining the score by formula (I):

$$\text{Logit } P = -4.762 + (2.852 \times \text{miR-155/miR-150}) + (0.337 \times \text{miR-378/miR-150}) + (1.276 \times \text{miR-636/miR-150}) + (1.578 \times \text{miR-19}b\text{-1/miR-378}).$$

5. The method of claim 1, wherein the human is a patient receiving dialysis treatment.

6. The method of claim 1, wherein the treatment is the chemotherapy and the ureteral resection surgery, administrating the chemotherapy and then administrating the ureteral resection surgery when a patient has stage III or stage IV tumor.

* * * * *